United States Patent [19]

Dawson et al.

[11] Patent Number: 5,709,089
[45] Date of Patent: Jan. 20, 1998

[54] PACKAGE FOR COOLING CONTAINING SUPERABSORBENT POLYMER

[76] Inventors: Gregory D. Dawson, 24 S. Monterey St., Mobile, Ala. 36604; Jonathan S. Browne, 204 Morgan Ave., Mobile, Ala. 36606

[21] Appl. No.: 610,217

[22] Filed: Mar. 4, 1996

[51] Int. Cl.$^6$ ........................................ F25D 5/00
[52] U.S. Cl. ........................................ 62/4; 126/263
[58] Field of Search .......................... 62/4; 126/263

[56] References Cited

U.S. PATENT DOCUMENTS

| | | | |
|---|---|---|---|
| 3,066,847 | 12/1962 | Fortune | 62/4 |
| 3,559,416 | 2/1971 | Cornwall | 62/4 |
| 4,181,285 | 1/1980 | Vangedal-Nielsen | 249/61 |
| 4,404,820 | 9/1983 | Romaine | 62/530 |
| 4,596,250 | 6/1986 | Beisang et al. | 128/402 |
| 4,780,117 | 10/1988 | Lahey et al. | 62/4 |
| 4,856,651 | 8/1989 | Francis, Jr. | 206/219 |
| 5,031,418 | 7/1991 | Hirayama et al. | 62/530 |
| 5,035,241 | 7/1991 | Walasek et al. | 128/403 |
| 5,054,290 | 10/1991 | Hogan | 62/45.1 |
| 5,150,707 | 9/1992 | Anderson | 128/402 |
| 5,263,479 | 11/1993 | Tesch | 607/114 |
| 5,271,244 | 12/1993 | Staggs | 62/457.3 |
| 5,393,462 | 2/1995 | Avery | 252/315.5 |
| 5,417,276 | 5/1995 | Dobry | 165/10 |
| 5,447,532 | 9/1995 | Furuya | 607/114 |

OTHER PUBLICATIONS

"*Thermonics Incorporated*"; 4513 Old Shell Road, Mobile, AL 36608.

*Primary Examiner*—Ronald C. Capossela
*Attorney, Agent, or Firm*—David L. Ray

[57] ABSTRACT

A package for cooling containing a superabsorbent polymer, the package including a bag for receiving and containing a liquid, the bag having an opening therein for receiving liquid medium, the bag being constructed of a material which is water impermeable, the bag having an inside and an outside, a pouch for holding a superabsorbent polymer, the pouch being connected to the inside of the bag, the pouch having a water permeable portion for enabling water to enter the pouch, and a superabsorbent polymer located inside the pouch.

20 Claims, 2 Drawing Sheets

5,709,089

1
PACKAGE FOR COOLING CONTAINING SUPERABSORBENT POLYMER

BACKGROUND OF THE INVENTION

1. Field of the Invention

The invention relates to cooling packages which may be frozen for cooling various products. In particular, the invention relates to cooling packages containing superabsorbent polymers for absorbing water.

2. Description of the Related Art

Cooling packages containing superabsorbent polymers which absorb large amounts of water are known in the art. U.S. Pat. No. 5,031,418 discloses a cooling packages utilizing a superabsorbent polymer as one element therein.

Superabsorbent polymers are water swellable gel-forming polymers which will absorb at least ten times their weight, although some superabsorbent polymers may absorb several hundred times their weight in water. Such superabsorbent polymers include starch-graft polymers, cross-linked glycolate and cellulose ethers, and gel-forming polyacrylates and polyvinylethers.

Such superabsorbent polymers may be in powdery form. It is believed that superabsorbent polymers owe their absorbency to carboxylic groups located on the spine of the polymer. When an aqueous medium contacts the polymer, the carboxylic groups are believed to solvate rapidly and develop mutually repulsive negative charges causing the polymer to uncoil and absorb many times its weight of the liquid medium (such as water) in which it is located. Crosslinking is believed to prevent the polymer from dissolving into solution with the liquid medium. The liquid medium such as water is believed to become oriented on the polymer's surface by virtue of hydrogen bonding, and the resulting gel has the ability to hold the liquid medium even under pressure.

After water is absorbed by the superabsorbent polymer, the weight and volume of the package containing the superabsorbent polymer greatly increases. Individual packets of superabsorbent polymer sandwiched between a layer of water impermeable material and a layer of water permeable material are known in the art and are sold by Thermonics Incorporated, 4513 Old Shell Road, Mobile, Ala. 36608 under the name Superfreeze®. Superfreeze® refrigerant pads may be placed in water to allow the superabsorbent polymer therein to absorb water, and then freezing the pad. The pads may then be placed on a product to cool the product.

Exemplary of additional patents of the related art are the following U.S. Patents: U.S. Pat. Nos. 4,404,820; 4,596,250; 4,856,651; 5,035,241; 5,054,290; 5,150,707; 5,263,479; 5,271,244; 5,393,462; 5,417,276; and 5,447,532.

SUMMARY OF THE INVENTION

In accordance with the present invention there is provided a package for cooling containing a superabsorbent polymer, the package including a bag for receiving and containing a liquid, the bag having an opening therein for receiving a liquid medium, the bag being constructed of a material which is water impermeable, the bag having an inside and an outside, a pouch for holding a superabsorbent polymer, the pouch being connected to the inside of the bag, the pouch having a water permeable portion for enabling water to enter the pouch, and a superabsorbent polymer located inside the pouch.

2
BRIEF DESCRIPTION OF THE DRAWINGS

DESCRIPTION OF THE PREFERRED EMBODIMENTS

Figure 1:
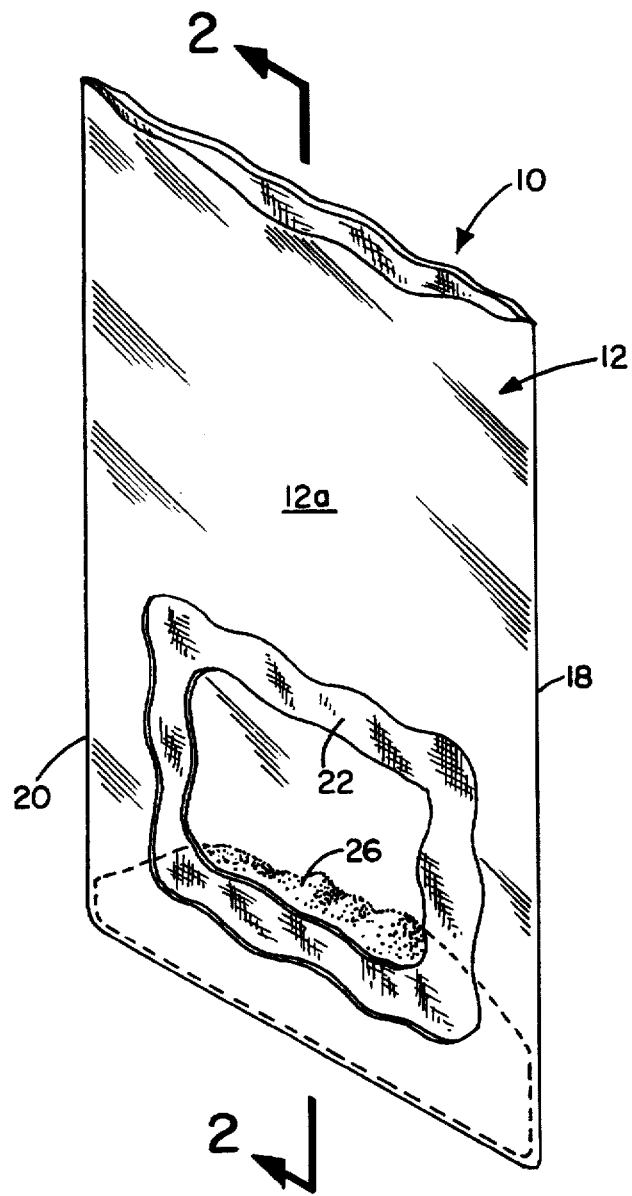
FIG. 1 is a partly cut-away, perspective view of the cooling package of the invention.
Figure 2:
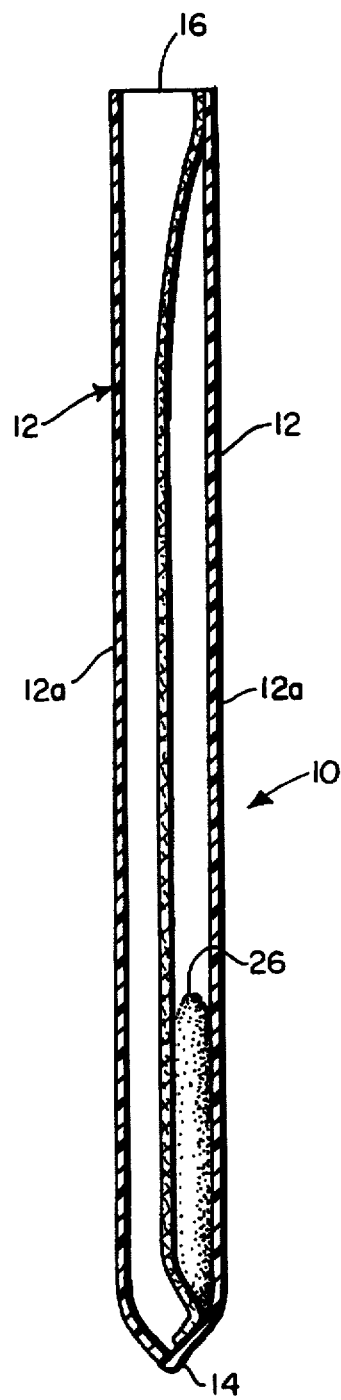
FIG. 2 is cross-sectional view of the cooling package of the invention taken along line 2—2 of FIG. 1.

Referring now to the drawings, the cooling package of the invention is generally indicated by the numeral 10. Package 10 can be seen in the drawings to include a hollow bag 12 having side walls 12a. The sides or walls of bag 12 are water impermeable and are preferably constructed from thermoplastic or thermosetting polymeric materials such as polyethylene, polyvinyl chloride, polyacrylates, and the like. Bag 12 is sealed at its bottom along seam 14 and is open at its top end 16. Preferably, bag 12 and cooling package 10 are generally rectangular in shape.

Bag 12 may be formed in any desired manner. Bag 12 could be formed by sealing two rectangular sheets of water impermeable plastic together at seam 14 and sides 18 and 20, or bag 12 could be extruded as a cylinder and sealed along bottom seam 14.

Connected to the inside of bag 12 is a water impermeable sheet 22. Sheet 22 forms a pouch or cell for the receipt and containment of superabsorbent polymer 26 and gel 30 between sheet 22 and side wall 12a. Sheet 22 is shown in the drawings to be preferably generally rectangular in shape, although any desired shape may be used if desired. Sheet 22 is preferably constructed from a nonwoven fabric material. Preferably sheet 22 is resistant to tearing when frozen against another surface.

The entire outer edges 24 of sheet 22 are sealed to the inside of bag 12 after a superabsorbent polymer 26 such as "Sunwet IM-5700-D" manufactured by Sanyo Chemical K.K. is placed between the inside of sheet 22 and the inside of the portion of the bag 12 to which sheet 22 is attached. Preferably polymer 26 is in a dry, powdery form.

Sheet 22 may be attached to the inside of bag 12 by any method known in the art for attaching a nonwoven fabric or liquid permeable sheet to a liquid impermeable sheet, such as heat sealing, gluing or the like. When bag 12 is made from two rectangular sheets sealed at edges 18 and 20, sheet 22 may be attached to one of the two rectangular sheets from which bag 12 is formed as bag 12 is being formed.

Figure 3:
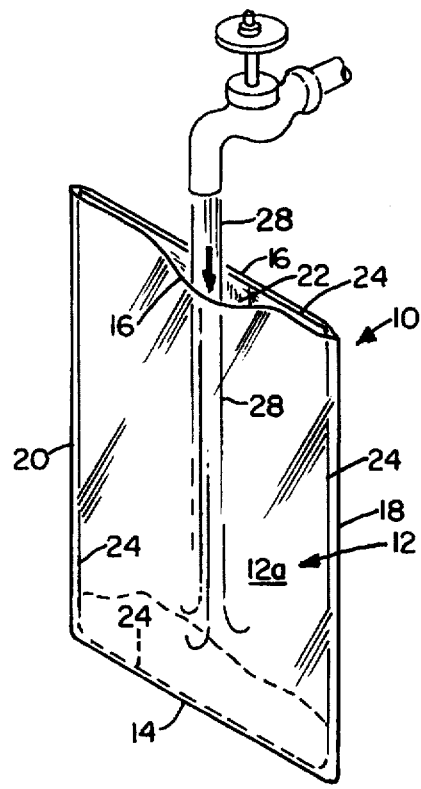
FIG. 3 is a perspective view of the cooling package of the invention being filled with water.
Figure 4:
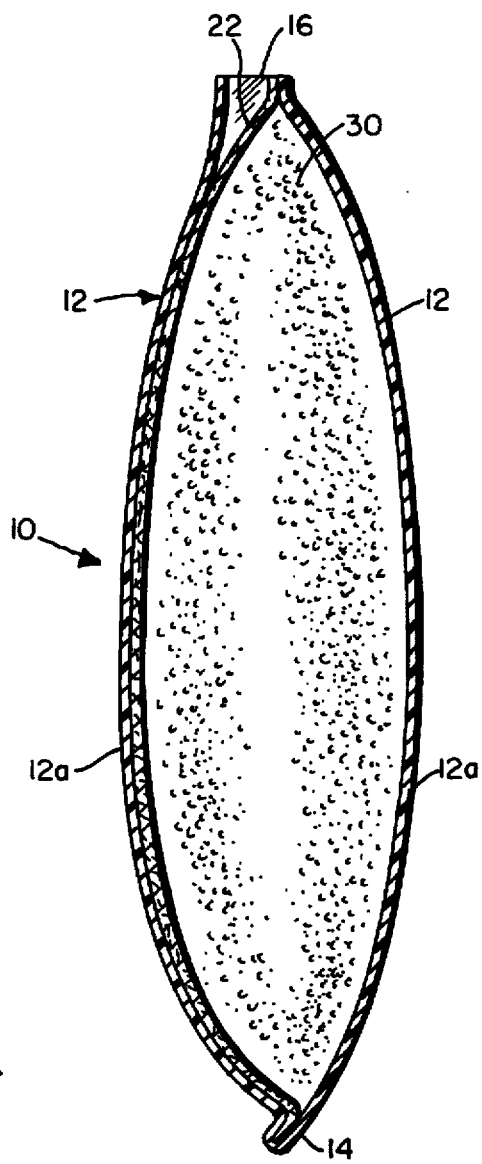
FIG. 4 is a cross-sectional view of the cooling package of the invention shown in FIG. 5 after the superabsorbent polymer therein has absorbed water and expanded.
Figure 5:
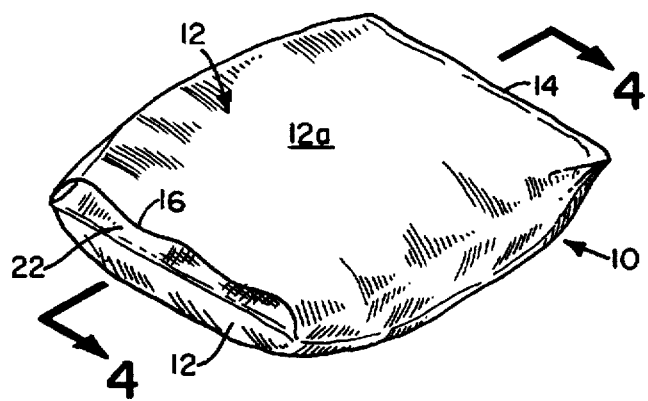
FIG. 5 is a perspective view of the cooling package of the invention shown in FIG. 1 after the superabsorbent polymer has absorbed water and expanded.

To cool commercial items such as perishable meats, vegetables, pharmaceuticals, candies, or the like, or consumer items such as soft drinks, sandwiches using the cooling package 10 of the invention, water 28 is introduced into the interior of cooling package 10 through the open top end 16 of cooling package 10 as shown in FIG. 3. The dry, powdery superabsorbent polymer 26 absorbs water 28 and swells to become gel 30 shown in FIG. 4. Cooling package 10 assumes the shape shown in FIG. 5.

The top 16 of cooling package 10 remains open after adding water to bag 12. Any excess water not absorbed by superabsorbent polymer 26 may be poured from cooling package 10. Cooling package 10 may then be frozen and placed in an ice chest to cool the items therein, or placed on or in the close vicinity of any other article which is desired to be cooled. When the ice in cooling package melts, the resultant water remains encapsulated in gel form within cooling package 10. Therefore, there is no water to contaminate or to be absorbed by items contained in the ice chest or other container in which cooling package 10 was placed.

There is no need to soak the cooling package 10 in water before freezing. Water may be introduced into cooling package 10 while cooling package 10 is in the vertical position as shown in FIG. 3. The cooling packages 10 may be stacked vertically in a freezer while the superabsorbent polymer 26 is still absorbing the water in bag 12 and forming a gel, because bag 12 prevents leakage of water prior to entering the freezer prior to absorption of the water by superabsorbent polymer 26.

Bag 12 encloses most, if not all the water permeable sheet 22 and prevents tearing of sheet 22. Water will be absorbed quickly by the superabsorbent polymer 26 and the cooling package 10 may be placed in a freezed for freezing. After use, the cooling package 10 may be discarded.

The cooling packages 10 of the invention may be packed compactly in a box or placed on a roll for storage before adding water to the superabsorbent polymer and freezing the cooling package.

Although the preferred embodiments of the invention have been described in detail above, it should be understood that the invention is in no sense limited thereby, and its scope is to be determined by that of the following claims:

What is claimed is:

1. In a package for cooling containing a superabsorbent polymer, the improvement comprising:
   a. a bag for receiving and containing a liquid, said bag having an opening therein for receiving said liquid, said bag being constructed of a material which is liquid impermeable, said bag having an inside and an outside,
   b. a pouch for holding a superabsorbent polymer, said pouch being connected to the inside of said bag, said pouch having a water permeable portion for enabling said liquid to enter said pouch, and
   c. a superabsorbent polymer located inside said pouch.

2. The package of claim 1 wherein said liquid is water.

3. The package of claim 2 wherein said package is generally rectangular in shape.

4. The package of claim 3 wherein said bag is generally rectangular in shape.

5. The package of claim 4 wherein said pouch is generally rectangular in shape.

6. The package of claim 5 wherein said pouch is constructed from a nonwoven fabric.

7. The package of claim 1 wherein said package is generally rectangular in shape.

8. The package of claim 1 wherein said bag is generally rectangular in shape.

9. The package of claim 1 wherein said pouch is generally rectangular in shape.

10. The package of claim 1 wherein said pouch is constructed from a nonwoven fabric.

11. The package of claim 1 wherein said bag is constructed from a polymeric material.

12. The package of claim 1 wherein said bag is constructed from a polymeric material.

13. In a package for cooling containing a superabsorbent polymer, the improvement comprising:
   a. a bag for receiving and containing a liquid, said bag having side walls and a top end and a bottom end, said bag having an opening in the top end thereof for receiving said liquid, said bag being closed at the bottom end thereof, said bag having an inside and an outside, said bag being constructed of a material which is liquid impermeable,
   b. a water permeable sheet for holding a superabsorbent polymer, said sheet being connected at its edges to said inside of said sidewalls of said bag, and
   c. a superabsorbent polymer located inside between said liquid impermeable sheet and said sidewalls.

14. The package of claim 13 wherein said liquid is water.

15. The package of claim 14 wherein said package is generally rectangular in shape.

16. The package of claim 13 wherein said package is generally rectangular in shape.

17. The package of claim 13 wherein said bag is generally rectangular in shape.

18. The package of claim 13 wherein said water permeable sheet is generally rectangular in shape.

19. The package of claim 13 wherein said water permeable sheet is constructed from a nonwoven fabric.

20. The package of claim 13 wherein said bag is constructed from a polymeric material.

* * * * *